United States Patent [19]

Morgan

[11] Patent Number: 4,923,447

[45] Date of Patent: May 8, 1990

[54] SYRINGE ASSEMBLY

[76] Inventor: Michael W. Morgan, 191 Nancy La., Greenwood, Ind. 46142

[21] Appl. No.: 312,661

[22] Filed: Feb. 17, 1989

[51] Int. Cl.$^5$ .............................................. A61M 5/32
[52] U.S. Cl. ..................................... 604/198; 604/263
[58] Field of Search ................ 604/198, 192, 263, 187

[56] References Cited

U.S. PATENT DOCUMENTS 4,356,822 11/1982 Winstead-Hall .
4,573,976 3/1986 Sampson et al. .
4,631,057 12/1986 Mitchell .
4,702,739 10/1987 Milorad .............................. 604/198

FOREIGN PATENT DOCUMENTS 2079607 1/1982 United Kingdom ................ 604/198

Primary Examiner—John D. Yasko
Attorney, Agent, or Firm—Thomas & Kennedy

[57] ABSTRACT

A syringe assembly comprises an elongated tubular syringe barrel having a tubular needled mounted to one end and a plunger slidably disposed within the barrel. A hollow outer casing is mounted to and surrounds the syringe barrel with the barrel and the casing defining an interior space therebetween. A tubular sleeve is telescopically disposed within the space between the casing and barrel and is movable between an extended position surrounding and shielding the syringe needle and a retracted position in which the needle is exposed for use. A longitudinal slot is formed in the casing and a projection mounted to the sleeve is slidably disposed within the slot to function as a lever for moving the sleeve between its extended and retracted positions. Notches are formed on either end of the slot such that the projection can be moved laterally into a notch to lock the sleeve in either its extended or its retracted position.

6 Claims, 2 Drawing Sheets

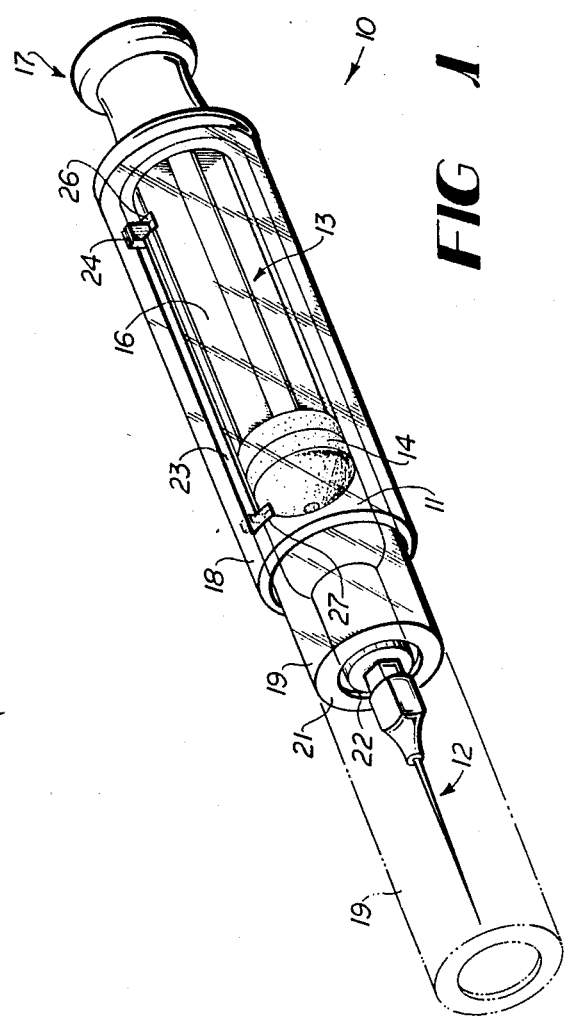
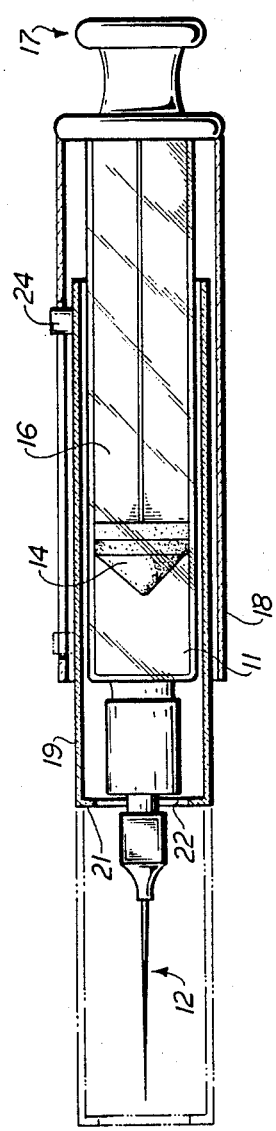
FIG. 1
FIG. 2

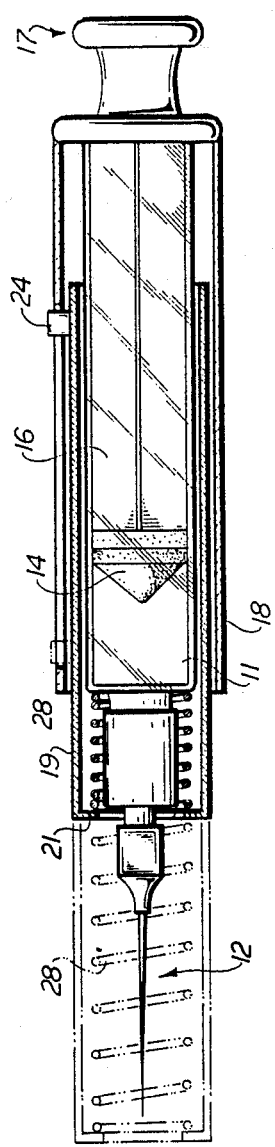
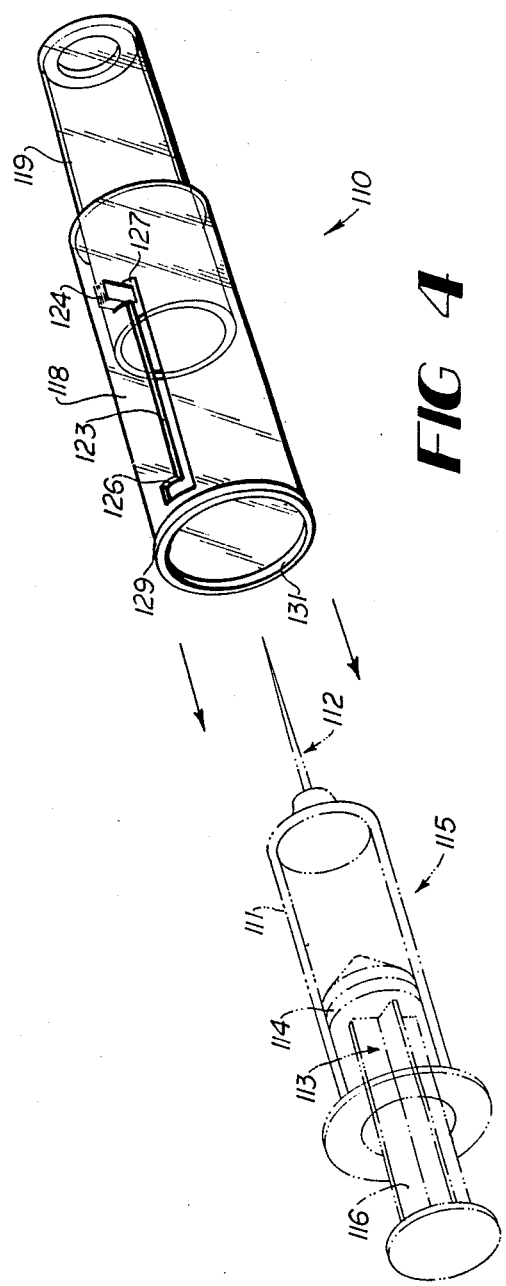
FIG 3
FIG 4

SYRINGE ASSEMBLY

TECHNICAL FIELD

The present invention relates to syringes and, more particularly, to a syringe assembly having a needle shield for preventing unintended human contact with the syringe needle.

BACKGROUND OF THE INVENTION

The common medical syringe has been used for many years to inject medications and other fluids into the bloodstream of patients. Syringes are also used to aspirate or withdraw fluids, such as blood samples, from patients. Such syringes typically comprise a cylindrical syringe barrel having a tubular needle mounted to one end and a plunger slidably disposed within the barrel for injecting and aspirating fluids.

Once inserted into a patient's bloodstream, a syringe needle can and often does become contaminated with microscopic viruses or bacteria that may be present in the bloodstream. Such a contaminated needle can be extremely dangerous to medical personnel handling the syringe since an accidental needle prick or even contact with the exposed needle can infect them with the virus or bacteria present on the needle. This danger is particularly acute in emergency medical situations in which there is often no time to dispose of contaminated needles carefully and properly.

Many cases of infection of medical personnel through accidental contact with contaminated syringe needles are documented each year. Sometimes, doctors and nurses who are accidentally pricked or contact a contaminated needle contract fatal diseases such as hepatitis and, more recently, Acquired Immune Deficiency Syndrome (AIDS).

Attempts have been made to reduce the dangers of contaminated syringe needles. Most commonly, the needle is simply covered with a plastic cap which fits over the needle and can be removed for use and replaced after use. This solution is often unsatisfactory since the nurse or doctor must manually place the cap back over the end of the needle. Many accidental pricks and contact with contaminated needles have occurred while attempting to replace the cap over the contaminated needle.

Other attempts to solve these problems are illustrated by U.S. Pat. Nos. 4,356,822; 4,573,976 and 4,631,057. These patents, in general, show specially made syringes having external telescoping sleeves mounted about the syringe barrel and adapted to be telescoped outwardly to surround the needle and telescope inwardly to expose the needle. While these devices, in general, can reduce the risk of accidental contact with a contaminated needle, they require that the entire syringe be specially formed and manufactured with complex sliding and locking mechanisms which not only tend to interfere with the use of the syringe, but can also be prohibitively expensive to manufacture relative to the common syringe. Further, these devices are not usable with a standard syringe to address the problems related to accidental contact.

A continuing need exists, therefore, for a simple to operate, efficient and inexpensive method of preventing accidental contact with contaminated syringe needles that can also be used with standard syringes. It is to the provision of such a method and apparatus that the present invention is primarily directed.

SUMMARY OF THE INVENTION

The present invention is a syringe assembly adapted to prevent accidental or unwanted contact with the needle of a syringe. In one embodiment, the apparatus comprises a syringe having a syringe barrel, a tubular needle, and a plunger slidably disposed within the barrel. A clear plastic casing is concentrically mounted about the syringe barrel to define a space between the barrel and the casing. Slidably disposed within the space is a cylindrical plastic needle shield comprising a sleeve which can be moved telescopically between an extended position surrounding and limiting access to the needle and a retracted position exposing the needle for use.

The outer casing has a longitudinally extending slot formed therein and the sleeve bears a small projection which extends radially outwardly from the sleeve through the slot in the casing. The sleeve can thus be moved between its extended and retracted positions by sliding the projection within the casing slot. A transversely extending notch is formed at each end of the slot with the notches sized to receive the projection such that when the projection is moved to the extreme ends of the slot, it can be moved transversely into one of the notches thereby locking the sleeve either in its extended or retracted position.

In a separate embodiment, the casing and telescoping shield are formed as an attachment adapted to be mounted to the barrel of a standard syringe and, once mounted, to function as just described.

Thus, it is seen that a device for preventing accidental contact with contaminated syringe needles is now provided which is inexpensive to produce, simple to operate and can be used with standard syringes. When a doctor, nurse or other medical personnel wishes to use the syringe, he or she simply slides the projection rearwardly within the slot to move the sleeve to its retracted, needle exposing position. After use, the projection is slid forwardly within the slot moving the sleeve to its extended needle shielding position whereupon the projection is simply moved laterally into the transversely extending notch, thereby locking the shield in its extended position. The syringe can then be handled or discarded without fear of accidental contact with the needle. Additional features, advantages and objects of the invention will become apparent upon reading the following detailed description with reference to the accompanying drawings.

BRIEF DESCRIPTION OF THE DRAWINGS

FIG. 1 is perspective view of a syringe which embodies the principles of the present invention in a preferred form.

FIG. 2 is a side elevational view of the syringe of FIG. 1 showing the needle shield in its retracted position in solid lines and, in phantom lines, in its extended position.

FIG. 3 is a side elevational view of a second embodiment of the invention having a spring actuated needle shield.

FIG. 4 is a perspective view of a third embodiment of the invention adapted to be mounted to a standard syringe.

DETAILED DESCRIPTION

Referring now in more detail to the drawings in which like numerals represent like parts throughout the several views, FIG. 1 shows a syringe assembly 10 having an elongated cylindrical syringe barrel 11 and a tubular syringe needle 12 mounted to one end of the barrel with the needle communicating with the interior portion of the barrel. A plunger 13 includes a plunger arm 16 having a rubberized piston 14 mounted to its interior end portion. The piston 14 is slidably disposed within th syringe barrel and the outer end 17 of the plunger arm is formed to facilitate longitudinal manual movement of the plunger and piston within the syringe barrel 11. Fluid can thus be aspirated through the needle and into the syringe barrel by moving the plunger rearwardly and injected from the syringe barrel through the needle by moving the plunger forwardly.

A cylindrical hollow casing 18 is mounted to and surrounds the syringe barrel. The interior diameter of the casing 18 is greater than the diameter of the syringe barrel such that the casing and barrel together define an interior space therebetween. Telescopically disposed within the interior space between the casing and the barrel is a cylindrical hollow sleeve 19. The sleeve 19 is telescopically movable relative to the casing between an extended position surrounding and shielding the needle 12 and a retracted position exposing the needle 12 for use. In FIG. 1, the sleeve 19 is shown in solid lines in its retracted position and in phantom lines in its extended position. A lip 21 extends radially inwardly from the exterior end of the sleeve 19 to define an orifice 22 sized to pass the needle 12.

A longitudinally extending slot 23 is formed in the casing 18 and the interior end portion of the sleeve 19 includes a radially extending projection 24 which is slidably disposed within the slot 23. The projection 24 functions as a lever such that the sleeve 19 can be moved between its extended and retracted positions by sliding the projection 24 longitudinally within the slot 23. When the sleeve 19 is in its fully extended position, as shown in phantom lines in FIG. 1, the projection 24 rests within the slot adjacent its front end portion. Conversely, when the sleeve 19 is in its fully retracted position, as shown in solid lines in FIG. 1, the projection 24 rests within the slot adjacent the rear end portion thereof.

A notch 26 is formed in the casing 18 adjacent the rear end portion of the slot 23 and extends substantially transversely relative to the slot. Similarly, a notch 27 is formed at the front end portion of the slot 23 and also extends substantially transversely relative thereto. The notches 26 and 27 are each sized to receive the projection 24 upon its being moved from an end portion of the slot 23 transversely into the notch. Thus, it is seen that the notches 26 and 27 cooperate with the projection 24 to provide locking mechanisms for releasibly locking the sleeve 19 in either its extended or its retracted position.

In operation, the sleeve 19 is extended by pushing the projection 24 forwardly within the slot and locked in its extended position by moving the projection 24 transversely into the forward notch 27. Conversely, the sleeve 19 can be locked in its retracted position by sliding the projection rearwardly to the back end portion of the slot 23 and moving the projection laterally into the rear notch 26. When the sleeve 19 is locked in its extended needle shielding position, medical personnel are protected from accidental pricks from and accidental contact with the needle even if the syringe assembly rolls off of a table and falls needle first onto, for example, the top of a foot.

FIG. 3 shows an alternate embodiment of the syringe assembly in which a coil spring 28 is positioned to bias the sleeve 19 toward its extended needle shielding position. The spring 28 bears at one end against the front end portion of the syringe barrel 11 and, at its other end, against the inwardly extending lip 21 of the sleeve 19. In the retracted position of the sleeve 19, as shown in the solid lines of FIG. 3, the coil spring 28 is compressed. The sleeve 19 can be locked in its retracted position by sliding the projection 24 laterally into notch 26 for use of the syringe. When unlocked, the coil spring 28 causes the sleeve 19 to telescope forwardly to its extended position as shown in phantom lines as in FIG. 3. In this position, an injection can be administered by placing the end of the sleeve 19 against the patient's skin and moving the syringe assembly forward. This causes the sleeve 19 to retract against the bias of the coil spring such that the needle 12 can enter the patient's body in the usual way. When removed from the patient's body, the coil spring urges the sleeve 19 back to its extended position such that a potentially contaminated needle is never exposed and is, at all times, shielded by the sleeve 19.

FIG. 4 shows an alternate embodiment of the invention for use as an accessory or attachment to a conventional syringe. A conventional syringe 115, shown in phantom lines, is seen to have a hollow syringe barrel 111 to the end of which is mounted a tubular needle 112. A plunger 113 having a plunger arm 116 and a piston 114 is slidably disposed within the syringe barrel 111 for injection and aspiration of fluids from within the syringe barrel in the usual way.

The needle shield assembly 110 is seen to comprise a cylindrical outer casing 118 and a cylindrical sleeve 119 telescopically mounted within the casing 118. A longitudinally extending slot 123 is formed in the casing 118 and a pair of notches 126 and 127 extend transversely from the slot 123 at the ends thereof. The sleeve 119 has a radially extending projection 124 which is slidably disposed within the slot 123. As with the embodiments of FIGS. 1–3, the sleeve 119 can be extended and retracted by moving the projection 124 longitudinally within the slot 123. Also, the sleeve 119 can be releasibly locked in its extended or retracted position by moving the projection 124 transversely into one of the notches 126 or 127.

An annular grommet 129 is mounted about the rear end portion of the casing 118 with the grommet defining a circular opening 131 which communicates with the interior of the casing 118. Preferably, the grommet 129 is formed of resilient material such as latex rubber and the opening 131 is slightly smaller in diameter than the diameter of the syringe barrel 111. With this configuration, the needle shield 110 can be slid over the syringe barrel 111 such that the casing and the sleeve substantially surround the barrel. The grommet opening 131, being slightly smaller than the syringe barrel, grips the barrel tightly and maintains the needle shield securely in place about the syringe. Once in place, the needle shield can be operated as described above to shield the needle when the syringe is not in use and expose the needle for use when desired.

In the embodiments of FIGS. 1–4, both the casing and the sleeve are preferably formed of clear acrylic plastic such that the syringe and any fluids therein or markings thereon are easily visible through the needle shield assembly.

The invention has been described in terms of preferred embodiments. It will be obvious to those of skill in the art, however, that many modifications, deletions and additions could be made to these embodiments without departing from the spirit and scope of the invention as set forth in the claims.

I claim:

1. A syringe assembly comprising:
   an elongated tubular syringe barrel;
   a tubular needle mounted to said syringe barrel with the interior of said tubular needle being in fluid communication with the interior or said syringe barrel;
   plunger means movably positioned within said syringe barrel for aspirating or injecting fluid from said syringe;
   a hollow casing mounted to said syringe barrel with said casing and said syringe barrel defining an interior space therebetween;
   needle shielding means comprising a tubular sleeve movably positioned within said interior space and surrounding said syringe barrel with said sleeve being movable between an extended position surrounding and shielding said needle and a retracted position in which said needle is exposed for use;
   said syringe barrel, said casing and said sleeve being substantially cylindrical and coaxial and said sleeve being telescopically disposed within said interior space;
   said casing being formed with a longitudinally extending slot and said sleeve including a radially extending projection slidably disposed within said slot, whereby said sleeve can be moved between its extended and retracted positions by sliding said projection within said slot.

2. The syringe assembly of claim 1 further comprising locking means for releasibly locking said tubular sleeve in its extended position and in its retracted position.

3. The syringe assembly of claim 2 wherein said locking means comprises a notch formed in said casing at each end of said slot with each notch being disposed substantially transversely relative to said slot and sized to receive said projection.

4. A needle shield for use with a syringe of the type having a substantially cylindrical hollow syringe barrel, a tubular needle mounted to one end of the syringe barrel and communicating with the interior thereof and a plunger movable disposed within said syringe barrel for aspirating or injecting fluid from the syringe, said needle shield comprising:
   a substantially cylindrical casing adapted to be mounted to and surround the syringe barrel with said casing having a longitudinally extending slot formed therein; and
   a substantially cylindrical hollow sleeve member telescopically disposed within said casing with said sleeve member being longitudinally movable between an extended position and a retracted position relative to said casing; and
   said sleeve member including a radially extending projection slidably disposed within said slot,
   whereby the casing can be mounted to a syringe and the sleeve member extended to surround and shield the needle when the syringe is not in use and retracted to expose the needle when the syringe is in use.

5. The needle shield of claim 4 further comprising locking means for releasibly locking said sleeve member in its extended and retracted positions.

6. The needle shield of claim 5 wherein said locking means comprises a notch formed in said casing on each end of said slot with each notch extending substantially transversely relative to said slot and being sized to receive said projection, whereby the sleeve member can be telescoped longitudinally relative to the casing to its extended or retracted position by moving its projection within the slot and, when in position, releasibly locked by moving the projection transversely into the adjacent notch.

* * * * *